(12) United States Patent
Grillberger et al.

(10) Patent No.: US 10,745,672 B2
(45) Date of Patent: *Aug. 18, 2020

(54) METHOD OF PRODUCING A POLYPEPTIDE OR VIRUS OF INTEREST IN A CONTINUOUS CELL CULTURE

(71) Applicants: Baxalta GmbH, Glattpark (Opfikon) (CH); Baxalta Incorporated, Bannockburn, IL (US)

(72) Inventors: Leopold Grillberger, Vienna (AT); Manfred Reiter, Vienna (AT); Daniel Fleischanderl, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,216

(22) Filed: Jan. 18, 2019

(65) Prior Publication Data

US 2019/0153400 A1  May 23, 2019

Related U.S. Application Data

(60) Continuation of application No. 15/486,181, filed on Apr. 12, 2017, now Pat. No. 10,221,400, which is a continuation of application No. 14/050,710, filed on Oct. 10, 2013, now Pat. No. 9,650,612, which is a division of application No. 12/847,921, filed on Jul. 30, 2010, now Pat. No. 8,580,554.

(60) Provisional application No. 61/230,313, filed on Jul. 31, 2009.

(51) Int. Cl.
| | |
|---|---|
| *C12N 7/00* | (2006.01) |
| *C12N 9/64* | (2006.01) |
| *C12P 21/02* | (2006.01) |
| *A61K 38/00* | (2006.01) |

(52) U.S. Cl.
CPC ............. *C12N 7/00* (2013.01); *C12N 9/6489* (2013.01); *C12P 21/02* (2013.01); *C12N 2710/00052* (2013.01); *C12Y 304/24087* (2013.01); *Y02P 20/52* (2015.11)

(58) Field of Classification Search
CPC .............. C12N 9/6489; C12N 2500/99; C12N 15/1135; C12N 5/0018; C12Y 304/24087; A61K 38/4886; C12P 21/00
USPC .............................. 435/212, 219, 70.3, 94.67
See application file for complete search history.

(56) References Cited

FOREIGN PATENT DOCUMENTS

| | | |
|---|---|---|
| JP | 2009-521941 A | 6/2009 |
| WO | WO 02/29083 A2 | 4/2002 |
| WO | WO 2006/133955 A1 | 12/2006 |
| WO | WO 2007/077217 A2 | 7/2007 |
| WO | WO 2009/086309 A2 | 7/2009 |

OTHER PUBLICATIONS

Antoine et al., "ADAMTS13 Gene Defects in Two Brothers with Constitutional Thrombotic Thrombocytopenic Purpura and Normalization of von Willebrand Factor-Cleaving Protease Activity by Recombinant Human ADAMTS13," British Journal of Haematology, vol. 120, No. 5, pp. 821-824, Mar. 1, 2003.
Banik et al., "Hybridoma Growth and Antibody Production as a Function of Cell Density and Specific Growth Rate in Perfusion Culture," Biotechnology and Bioengineering, vol. 48, No. 3, pp. 289-300, 1995.
Banik et al., Partial and total cell retention in a filtration-based homogeneous perfusion reactor. *Biotechnol. Prog.* 11(5): 584-8 (1995).
Batt et al., "Inclined Sedimentation for Selective Retention of Viable Hybridomas in a Continous Suspension Bioreactor," Biotechnology Progress, vol. 6, pp. 458-464, Jan. 1, 1990.
Cardoso et al., "Protein-Free Media for the Production of Infectious Bronchitis Virus ($M_{41}$) Strain in a Continuous Cell Line," ALTEX 2005, 22, pp. 152-156.
Castilho et al., "Cell Retention Devices for Suspended-Cell Perfusion Cultures," Advances in Biochemical Engineering, Biotechnology, vol. 74, pp. 129-169, Jan. 1, 2002.
Gorenflo et al., "Optimization of an Acoustic Cell Filter with a Novel Air-Backflush System," Biotechnology Progress, vol. 19, No. 1, pp. 30-36, Jan. 2003.
Hiller et al., "Cell Retention-Chemostat Studies of Hybridoma Cells: Analysis of Hybridoma Growth and Metabolism in Continuous Suspension Culture on Serum-Free Medium," Biotechnology and Bioengineering, vol. 42, No. 2, pp. 185-195, 1993.

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

Described herein is a chemostat-like continuous cell culture system that combines certain advantages of perfusion open systems and chemostat open systems to improve the culturing of mammalian cells, e.g., genetically modified cells, particularly in serum-free or chemically-defined media. The continuous culture system described herein involves culturing mammalian cells in a continuous cell culture system, which comprises a cell retention device, wherein the cell culture system has a dilution rate (D) of less than about 2 $d^{-1}$, and a cell density of less than about $2 \times 10^7$ cell/mL. Also described herein is a method for producing a polypeptide and/or virus of interest in a continuous cell culture, the method comprising culturing mammalian cells expressing the polypeptide and/or virus of interest in a continuous cell culture system, which comprises a cell retention device, wherein the cell culture system has a dilution rate (D) of less than about 2 $d^{-1}$, and a cell density of less than about $2 \times 10^7$ cell/mL; and recovering the polypeptide and/or virus of interest from medium of the cell culture system.

20 Claims, No Drawings

(56) References Cited

OTHER PUBLICATIONS

Kong et al., Long-term stable production of monocyte-colony inhibition factor (M-CIF) from CHO microcarrier perfusion cultures. *Cytotechnology*, 26: 131-8 (1998).

Leelavatcharamas et al., Use of cell cycle analysis to characterise growth and interferon-gamma production in perfusion culture of CHO cells. *Cytotechnology*, 30: 59-69 (1999).

Plaimauer et al., "Expression and Characterization of Recombinant Human ADAMTS-13," Seminars in Hematology, vol. 41, No. 1, pp. 24-33, Jan. 2004.

Ray et al., "Production of Genetically Modified Cells Expressing Specific Transgenes by Retroviral Vectors for Gene Thereapy," J. Tiss. Cul Meth 1993, 15, pp. 108115.

Robinson et al., "Effect of Specific Growth Rates on Productivity in Continuous Open and Partial Cell Retention Animal Cell Bioreactors," Journal of Biotechnology, vol. 22, No. 1-2, pp. 41-50, Jan. 1, 1992.

Schmid et al., "Continuous Hyrbidoma Suspension Cultures With and Without Cell Retention: Kinetics of Growth, Metabolism and Product Formation," Journal of Biotechnology, vol. 22, No. 1-2, pp. 31-40, Jan. 1, 1992.

Voisard et al., "Potential of Cell Retention Techniques for Large-Scale High-Density Perfusion Culture of Suspended Mammalian Cells," Biotechnology and Bioengineering, vol. 82, No. 7, pp. 751-765, Jun. 30, 2003.

Hayter, P., et al., "The Effect of the Dilution Rate on CHO Cell Physiology and Recombinant Interferon-y⁻ Production in Gucose-Limited Chemostat Culture", Biotechn. and Bioeng., v. 42, p. 1077-1085, 1993.

METHOD OF PRODUCING A POLYPEPTIDE OR VIRUS OF INTEREST IN A CONTINUOUS CELL CULTURE

CROSS REFERENCE TO RELATED APPLICATIONS

This application is a Continuation of U.S. patent application Ser. No. 15/486,181, filed Apr. 12, 2017, and issued as U.S. Pat. No. 10,221,400, which is a Continuation of U.S. patent application Ser. No. 14/050,710, filed Oct. 10, 2013, and issued as U.S. Pat. No. 9,650,612, which is a Divisional of U.S. patent application Ser. No. 12/847,921, filed Jul. 30, 2010, and issued as U.S. Pat. No. 8,580,554, which claims benefit of U.S. Provisional Application No. 61/230,313, filed Jul. 31, 2009, which are hereby incorporated by reference in their entireties, and to which applications we claim priority.

FIELD OF THE INVENTION

The present invention relates to a continuous cell culture strategy for producing polypeptides or viruses of interest in mammalian cell culture. The continuous cell culture strategy described herein combines the advantages of chemostat and perfusion culture technologies.

BACKGROUND OF THE INVENTION

The ability to produce a polypeptide or virus of interest is increasingly important to the biotechnology industry. Over the last two decades, advances in biotechnology have led to interest in numerous polypeptides and viruses that have potential therapeutic uses as vaccines and pharmaceuticals. Large scale production generally has involved recombinant production of the polypeptide or virus of interest, e.g., in bacterial, yeast, insect, mammalian, or other cell types. The production of polypeptides or viruses of interest in mammalian cultures, in particular, has advantages over production in bacterial or other lower microbial hosts because of the ability of mammalian cells to post-translationally process complex protein structures, via, e.g. disulfide-dependent folding and glycosylation.

Mammalian cells are generally propagated in vitro in one of two modes: as non-anchorage dependent cells growing freely in suspension throughout the bulk of the culture; or as anchorage-dependent cells requiring attachment to a solid substrate for their propagation (i.e., a monolayer type of cell growth). Microcarrier systems have been developed to accommodate both types of growth. For example, anchorage-dependent cells may be propagated in microcarrier systems comprising small solid particles suspended in growth medium by slow agitation. This system allows anchorage-dependent cells to attach to the surfaces of the suspended particles, and grow to confluency, while the microcarriers remain suspended in the growth medium. Alternatively, macroporous microcarriers may be used to contain non-anchorage dependent cells in bioreactors, e.g., by nonspecific attachment for the cells to the surface of such microcarriers. Microcarrier suspension cultures of either non-anchorage dependent cells or anchorage-dependent cells are the most widely used means of large scale production of cells and cell products.

Large-scale suspension cultures may be operated in a closed system, for example, as batch or fed-batch closed systems, which are more straightforward to operate and scale up than open systems. Typically, in a closed system, no cells, products, and/or waste products are removed (although air (e.g., oxygen) may be added and $CO_2$ removed by aeration). The typical growth profile seen with batch growth systems involves a lag phase, followed by an exponential phase, a stationary phase, and a decline phase. In such batch systems, the environment is continuously changing, as nutrients are depleted and metabolites accumulate. In a fed batch system, key nutrients are continuously fed into the system to prolong the growth cycle although cells, products, by products, and waste products, including toxic metabolites, are not removed. Accordingly, production of a polypeptide or virus of interest by the batch or fed batch systems is limited by the accumulation of cells and harmful substances, such as toxic metabolites.

Large-scale suspension cultures may also be operated in an open system, e.g., a perfusion system or a chemostat system. In a perfusion system, fresh medium is perfused through the culture while the cells are retained with a variety of cell retention devices. Types of cell retention devices include, for example, microcarriers, fine mesh spin filters, hollow fibers, flat plate membrane filters, settling tubes, ultrasonic cell retention devices, and the like. Typically, perfusion cultures are designed to increase cell densities to a maximum, with cell retention devices designed and operated to have a cell retention rate of >90%. Such cultures typically reach cell densities of $>2 \times 10^7$, which may have to be supplied with a cell culture medium feed at a dilution rate greater than about 2.0 $d^{-1}$. However, the steady state of the system is hard to maintain because of the uncontrolled increase in biomass, and consistent production conditions are difficult to control and/or achieve.

Chemostat systems are operated with a continuous inflow of medium and an outflow of cells and products. In the chemostat system, there is no cell retention device, such that the concentration of cells in the bioreactor and the concentration of the cells in supernatant harvested from the bioreactor are substantially identical. Typically, culture medium is fed to the reactor at a predetermined and constant rate, maintaining a low dilution rate of the culture (typically 0.3 $d^{-1}$ to 0.8 $d^{-1}$). To prevent washout of cells, the dilution rate generally is chosen to be less than, and sometimes equal to, the maximum specific growth rate of the cells. Culture fluids containing cells, cell products, byproducts, waste products, etc., are removed at the same rate, or substantially the same rate. Chemostat systems typically provide for a high degree of control, since the cultures may equilibrate, i.e., reach a steady state at a specific growth rate equivalent to the dilution rate. This equilibration is determinative of the concentration of the cells, metabolites, waste products, expressed products (e.g. secreted proteins), etc. Specific growth rates in chemostat systems are typically lower than the maximum growth rate due to at least one limiting substrate. In some systems, however, steady states may be maintained at the maximum specific growth rates by controlling and adjusting biomass, e.g., in turbidstat systems of chemostat cultures. Preferably, such chemostat cultures contain a homogeneous distribution of cells (e.g., single cell suspensions) throughout the bioreactor. Compared to the perfusion system, however, the chemostat system typically results in lower cell densities. Furthermore, an inherent disadvantage of chemostat systems is that the feed of the cells can not be controlled independent of the cell densities in the bioreactor system.

Suspension cell cultures for producing recombinant proteins in serum-free and/or chemically-defined media are also limited in that the serum-free and/or chemically-defined media typically support slower growth rates compared to cells grown in media containing serum. Lowered growth rates in the culture means a lowered production of the polypeptide or virus of interest.

Accordingly, there remains a need for the development of cell culture systems capable of sustaining production of a polypeptide or virus of interest, especially for cultures that can be sustained for prolonged periods of time, for example, to meet demands for increased production at low costs. The present invention provides methods and compositions directed at meeting this and other needs.

SUMMARY

Disclosed herein is a continuous cell culture for the production of polypeptides and/or viruses of interest in mammalian cells, particularly non-anchorage dependent cells. The continuous cell culture method disclosed herein combines advantages of perfusion open systems and chemostat open systems and allows for increased cell density and cell growth, particularly in serum-free or chemically-defined media. The increased cell density and cell growth provides for improved yields of proteins and/or viruses of interest while allowing more control over process parameters.

Accordingly, one aspect of the invention relates to a method for producing a polypeptide and/or virus of interest in a continuous cell culture, the method comprising culturing mammalian cells expressing the polypeptide and/or virus in a continuous cell culture system, wherein the cell culture system comprises a cell retention device and has a dilution rate of less than about 2 $d^{-1}$ and a cell density of less than about $2 \times 10^7$ cell/mL; and recovering the polypeptide and/or virus of interest from medium removed from the cell culture system. In some embodiments, the cells are genetically modified to recombinantly express the polypeptide and/or virus of interest.

In some embodiments, the cell retention device is chosen to be less capable of retaining cells than typical cell retention devices. In some embodiments, the cell retention device produces a cell retention rate of less than about 90%, less than about 85%, less than about 80%, or less than about 75%. In some embodiments, the cell retention device comprises a macroporous microcarrier, e.g., a cellulose-based particle.

The dilution rate and cell density preferably are maintained at chosen values or ranges. In some embodiments, the dilution rate is less than about 1 $d^{-1}$, e.g., between about 0.1 and about 1.0 $d^{-1}$. In some embodiments, the cell density is less than about $1 \times 10^7$ cell/mL. In some embodiments, the ratio of the dilution rate and the specific growth rate (D/μ) of the cell culture system is maintained at a chosen value or range. In some preferred embodiments, the cell culture system has a ratio of the dilution rate and specific growth rate greater than about 1, for example, between about 1.2 and about 5.0, or between about 1.8 and about 3. In some embodiments, the specific growth rate is maintained between 0.2 $d^{-1}$ and 0.8 $d^{-1}$.

An advantage of certain embodiments of the continuous cell culture system described herein is that the culture can be sustained for a prolonged period of time. In some embodiments, for example, the dilution rate and/or the cell density are maintained for at least about 80% of the time the cells are being cultured in the continuous cell culture system. In some embodiments, the cells are cultured in the cell culture system for more than 20 days, preferably more than 40 days, and more preferably, more than 50 days, for example, allowing increased production of the polypeptide and/or virus of interest, potentially at low cost.

Another advantage of certain embodiments of the continuous cell culture system is an increase in volumetric productivity due to higher cell density, compared to a typical chemostat culture. For example, in particular preferred embodiments, volumetric productivity increases by 70%, 90%, or more. Still another advantage of certain embodiments of the continuous cell culture system is improved specific activity of the protein being recovered, due to, for example, reduced residence time in the culture unit, which may have beneficial effect on stability, structure, and/or function of the protein.

Another advantage of certain embodiments of the continuous cell culture system described herein is that the system is amenable to being scaled up for large scale productions. That is, by allowing increased cell density and/or cell growth, as compared to standard chemostat culture systems, the continuous cell culture system disclosed herein provides for commercial scale production of a polypeptide and/or virus of interest. For example, in some embodiments, the cells are cultured in at least about 250 L of medium, e.g., at least abut 500 L, or at least about 1,000 L of medium. In some preferred embodiments, the cells are cultured in serum-free media and/or chemically-defined media.

In some embodiments, the method further comprises a pre-culturing step, e.g., to adapt the cells for production of the polypeptide and/or virus of interest in a continuous cell culture system as herein described. Thus, in some preferred embodiments, the method further comprises, before the culturing step, pre-culturing the cells in suspension, e.g., until the culture reaches an appropriate volume.

In a particular embodiment, the polypeptide of interest is a disintegrin-like and metallopeptidase with thrombospondin type 1 motif 13 (ADAMTS13) protein. In some embodiments, the mammalian cells are CHO cells, e.g., CHO cells genetically modified to express ADAMTS13 protein. In a particular embodiment, a method is provided for producing a polypeptide and/or virus of interest in a continuous cell culture, the method comprising (a) culturing non-anchorage dependent mammalian cells expressing the polypeptide and/or virus of interest in a continuous cell culture system, where the cell culture system comprises a cell retention device having a cell retention rate of less than 90%, and has a dilution rate (D) between 0.1 and 1.0 $d^{-1}$ and a cell density of less than $1 \times 10^7$ cell/mL; and (b) recovering the polypeptide and/or virus of interest from medium removed from the cell culture system.

In another particular embodiment, a method is provided for producing a polypeptide and/or virus of interest in a continuous cell culture, the method comprising (a) culturing non-anchorage dependent cells CHO cells expressing the polypeptide and/or virus of interest in a continuous cell culture system, where the cell culture system comprises a macroporous microcarrier cell retention device having a cell retention rate of less than 90%, and has a dilution rate (D) between 0.1 and 1.0 $d^{-1}$ and a cell density of less than $1 \times 10^7$ cell/mL; and (b) recovering the polypeptide and/or virus of interest from medium removed from the cell culture system.

In still another particular embodiment, a method is provided for producing ADAMTS13 in a continuous cell culture, the method comprising (a) culturing non-anchorage dependent cells mammalian cells expressing recombinant ADAMTS13 protein in a continuous cell culture system, where the cell culture system comprises a macroporous microcarrier cell retention device having a cell retention rate of less than 90%, and has a dilution rate (D) between 0.1 and 1.0 d$^{-1}$ and a cell density of less than 1×10$^7$ cell/mL; and (b) recovering the ADAMTS13 from medium removed from the cell culture system.

In yet another particular embodiment, a method is provided for producing a polypeptide and/or virus of interest in a continuous cell culture, the method comprising (a) culturing non-anchorage dependent cells mammalian cells expressing the polypeptide and/or virus of interest in a continuous cell culture system, where the cell culture system comprises a cell retention device having a cell retention rate of less than 90%, and has a dilution rate (D) between 0.1 and 1.0 d$^{-1}$, a cell density of less than 1×10$^7$ cell/mL, and a ratio of the dilution rate and specific growth rate (D/g) between 1.2 and 5; and (b) recovering the polypeptide and/or virus of interest from medium removed from the cell culture system; and further where the cells are cultured in the cell culture system for more than 50 days, and the dilution rate, cell density, and ratio of the dilution rate and specific growth rate each are maintained for at least 80% of the time the cells are cultured in the cell culture system.

A further aspect of the invention relates to a composition comprising a polypeptide and/or virus of interest produced according to methods described herein, e.g., a composition comprising a recombinant ADAMTS13 protein produced accordingly.

These and other aspects of the invention are described in more detail below.

DETAILED DESCRIPTION

The continuous cell culture system as described herein combines some of the advantages of both perfusion culture and chemostat culture of mammalian cells. As described above, perfusion culture systems are operated with fresh medium perfusing through the cell culture, while the cells are retained using a cell retention device; chemostat culture systems are operated with a continuous inflow of media and outflow of cells and products, without a cell retention device.

As used herein "perfusion" refers to continuous flow of a physiological nutrient solution at a steady rate, through or over a population of cells. As perfusion systems generally involve the retention of the cells within the culture unit, perfusion cultures characteristically have relatively high cell densities, but the culture conditions are difficult to maintain and control. In addition, since the cells are grown to and then retained within the culture unit at high densities, the growth rate typically continuously decreases over time, leading to the late exponential or even stationary phase of cell growth. In contrast, "chemostat" as used herein, refers to continuous inflow of a physiological nutrient solution coupled with a continuous outflow of cells and other products with withdrawn media, through a cell culture, e.g., as in chemostat systems. However, because cells are continuously removed, the chemostat system typically supports only lower cell densities.

The continuous culture strategy described herein generally comprises culturing mammalian cells, e.g., non-anchorage dependent cells, expressing a polypeptide and/or virus of interest during a production phase in a continuous cell culture system. By "non-anchorage dependent cells" is meant cells propagating freely in suspension throughout the bulk of a culture, as opposed to being attached or fixed to a solid substrate during propagation. The continuous cell culture system will comprise a cell retention device similar to that used in a perfusion system, but that allows continuous removal of a significant portion of the cells, preferably such that a smaller percentage of the cells are retained than in perfusion culture. By "cell retention device" is meant any structure capable of retaining cells, particularly non-anchorage dependent cells, in a particular location during cell culture. Nonlimiting examples include microcarriers, fine mesh spin filters, hollow fibers, flat plate membrane filters, settling tubes, ultrasonic cell retention devices, and the like, that can retain non-anchorage dependent cells within bioreactors. Polypeptides and/or viruses of interest (e.g., a recombinant polypeptide and/or recombinant virus) can be recovered from the cell culture system, e.g., from medium removed from the cell culture system.

The method for producing a polypeptide and/or virus of interest (e.g., a recombinant polypeptide and/or recombinant virus) disclosed herein comprises a cell culture method that provides a chemostat-like culture system and that uses a cell retention device. The system comprises culturing mammalian cells expressing a polypeptide and/or virus of interest in a continuous cell culture system with a cell retention device. The role of the cell retention device is to prevent the removal from culture a portion, preferably a substantial portion, of the viable cells during replenishment of the spent culture medium with fresh medium. A successful cell retention device should fulfill as many as possible of the following requirements: (1) minimal cell damage or effect on cell growth and productivity, (2) selective retention of viable cells only (nonviable cells preferably are removed from the culture since they release toxic metabolites into the culture environment), (3) uninterrupted operation for long periods of cultivation, (4) low energy consumption, (5) simplicity in operation and maintenance, (6) scale-up capabilities for large scale production units, (7) compact structure, and (8) cost effectiveness.

In particularly preferred embodiments, the cell retention device used permits partial retention of the cells. Cell retention devices and/or methods are well-known in the art. Many are based on conventional sedimentation, centrifugation, and/or filtration techniques. Nonlimiting examples of cell retention devices include microcarriers, spin filters, such as fine mesh spin filters, hollow fibers, flat plate membrane filters, settling tubes, ultrasonic cell retention devices, gravity settlers, centrifuges, acoustic cell filters, dielectrophoresis-based cell separators, and the like (see, e.g., U.S. Pat. Nos. 5,019,512; 5,626,734, which hereby are incorporated by reference in its entirety).

According to one embodiment of the culture system described herein, microcarriers may be used as the cell retention device. The microcarrier may act as a low cost scalable surface on which non-anchorage dependent cells may be immobilized in order to aid cell retention. As used herein, "microcarriers" refer to particles small enough to be used in suspension cultures, preferably with a stirring rate that does not cause significant shear damage to cells. Microcarriers may be solid, porous, or have a solid core with a porous coating. Microcarriers may, for example, without limitation, be cellulose- or dextran-based, and their surfaces (exterior and interior surface in case of porous carriers) may be positively charged. Further details regarding microcarriers can be found, e.g., in WO 02/29083, which hereby is incorporated by reference in its entirety.

In one embodiment, the microcarrier is a macroporous microcarrier. As used herein, "macroporous microcarriers" refers to particles, e.g. cellulose-based particles, which have the following properties: (a) they are small enough to allow use in suspension cultures, preferably with a stirring rate that does not cause significant shear damage to cells; and (b) they have pores and interior spaces of sufficient size to allow cells to migrate into the interior spaces. Their surfaces (exterior and interior) may in one embodiment be positively charged. In one embodiment, the carriers: (a) have an overall particle diameter between about 150 and about 350 µm; (b) have pores having an average pore opening diameter of between about 15 and about 40 m; and (c) have a positive charge density of between about 0.8 and 2.0 meq/g. In some embodiments, the positive charge is provided by DEAE (N,N,-diethylaminoethyl) groups. Useful macroporous microcarriers include, without limitation, CYTOPORE 1™ and CYTOPORE 2™ (GE Healthcare Life Sciences, Piscataway, N.J.). Particularly useful macroporous microcarriers are CYTOPORE 2™ carriers, which have a mean particle diameter of 230 µm, an average pore size of 30 µm, and a positive charge density of 1.8 meq/g.

In some embodiments, the culture units are agitated. Agitation may comprise shaking, stirring, rocking, vibrating, or the like, as known in the art. In a preferred embodiment, agitation is achieved with a Rushton type impeller with baffles. The baffles may be at about 140 rpm, which corresponds to a specific power/volume input of approximately 40 W/m$^3$. In some embodiments, the specific power/volume input is more than about 40 W/m$^3$, e.g., about 50 W/m$^3$, about 60 W/m$^3$, about 70 W/m$^3$, about 80 W/m$^3$ or more. Other speeds may be used as suitable according to the particular cells or culture being used.

The concentration of the microcarriers as described herein is generally low, for example, to aid in maintaining dilution rate and cell density in specific ranges. In one embodiment, the culture unit may comprise an amount of microcarriers corresponding to a final microcarrier concentration in the range of 0.05-1.0 g/L. In one embodiment, the final microcarrier concentration is about 0.05-0.1 g/L. In one embodiment, the final microcarrier concentration is about 0.1-0.25 g/L. In another embodiment, the final microcarrier concentration is about 0.25-0.5 g/L. In another embodiment, the final microcarrier concentration is about 0.5-0.75 g/L. In another embodiment, the final microcarrier concentration is about 0.75-1.0 g/L. In another embodiment the carrier concentration may be increased or reduced during the continuous culture, e.g., to adjust cell densities and dilution rates within predetermined ranges.

The disclosed continuous cell culture system has a preferred dilution rate (D) and a preferred cell density. In particular, the dilution rate and cell density are maintained at predetermined values or within predetermined ranges. Furthermore the disclosed continuous cell culture system may have a minimum specific growth rate or a predetermined range of specific growth rates over the entire process time.

Dilution rate (D) refers to the volume of medium supplied per day divided by the volume of the culture. Although the continuous cell culture system described herein involves cell retention, the dilution rate of the continuous cell culture system is generally less than that of a perfusion culture, e.g., less than about 2 dilution volume/day (2 d$^{-1}$). In one embodiment, the dilution rate is maintained between more than about 0.2 d$^{-1}$ to less than about 2.0 d$^{-1}$. In another embodiment, the dilution rate is maintained at less than about 2.0 d$^{-1}$, e.g., less than about 1.8 d$^{-1}$, e.g., less than about 1.5 d$^{-1}$, e.g., less than about 1.2 d$^{-1}$, etc. In another embodiment, the dilution rate is maintained at less than about 1.0 d$^{-1}$, e.g., less than about 0.9 d$^{-1}$, e.g., less than about 0.8 d$^{-1}$, e.g., less than about 0.7 d$^{-1}$, e.g., less than about 0.6 d$^{-1}$, etc. In another embodiment, the dilution rate is maintained at more than about 0.2 d$^{-1}$, e.g., more than about 0.3 d$^{-1}$, e.g., more than about 0.4 d$^{-1}$, e.g., more than about 0.5 d$^{-1}$, etc.

Additionally, in a continuous cell culture system as described herein, the cell density is maintained at a value less than that maintained in a perfusion culture system but higher than cell densities achieved in a chemostat system. In one embodiment, the cell density is less than about 2×10$^7$ cell/mL, e.g., less than about 1.5×10$^7$ cell/mL, e.g., less than about 1×10$^7$ cell/mL, e.g., less than about 8×10$^6$ cell/mL, e.g. less than about 6×10$^6$ cell/mL, e.g., less than about 5×10$^6$ cell/mL. In another embodiment, the cell density may be more than about 1×10$^6$ cell/mL, e.g., more than about 1.5×10$^6$ cell/mL, e.g. more than about 2×10$^6$ cell/mL, e.g. more than about 3×10$^6$ cell/mL, e.g. more than about 4×10$^6$ cell/mL, etc. In another embodiment, the cell density is maintained at between about 1.0×10$^6$ cell/mL to about 2×10$^6$ cell/mL. In another embodiment, the cell density is maintained at between about 2×10$^6$ cell/mL to about 4×10$^6$ cell/mL. In another embodiment, the cell density is maintained between about 5×10$^6$ cell/mL to about 1×10$^7$ cell/mL, e.g., between about 6×10$^6$ cell/mL to about 8×10$^6$ cell/mL. In another embodiment, the cell density is maintained between about 1×10$^7$ cell/mL to about 2×10$^7$ cell/mL.

A skilled artisan will recognize that a mechanism by which cell densities may be maintained involves decreasing the portion of cells retained with the cell retention device, i.e., the cell retention rate. Generally, a perfusion culture has a cell retention rate of greater than 90% or 95%, and, in many cases, close to 100%. In the disclosed continuous cell culture system, the cell retention rate is less than 90%. In one embodiment, the cell retention is less than about 85%, e.g., less than about 75%. In one embodiment, the cell retention rate is less than about 70%, e.g., less than about 60%, e.g., less than about 50%, e.g., less than about 40%, e.g., less than about 30%. In one embodiment, cell retention is maintained between about 30% and about 90%. In another embodiment, cell retention is maintained between about 30% and about 80%. In another embodiment, cell retention is maintained between about 30% and about 70%. In another embodiment, cell retention is maintained between about 40% and about 60%. In another embodiment, cell retention is maintained between about 40% and about 70%. In another embodiment, cell retention is maintained between about 50% and about 90%. In another embodiment, cell retention is maintained between about 60% and about 90%. In another embodiment, cell retention is maintained between about 70% and about 90%. In another embodiment, cell retention is maintained between about 80% and about 90%.

The culture may also be characterized by the ratio of the dilution rate and the specific growth rate. Specific growth rate (µ) refers to the increase in cell mass per cell mass per day (relative to the total cell mass): t=(ln($X_t$/$X_{t-1}$))/((t)−(t−1)); wherein $X_t$ is the biomass concentration at time (t) and $X_{t-1}$ is the biomass at previous timepoint. Generally, the specific growth rate of the continuous culture system as described herein should be constant within a predetermined range, and preferably with a certain minimum level to ensure a minimum of a growth-associated polypeptide and/or virus expression. For example, the specific growth rate of the continuous culture system described herein may be from about 0.1 d$^{-1}$ to about 1.0 d$^{-1}$. In one embodiment, the specific growth rate maintained by the continuous culture system described herein is greater than about 0.1 d$^{-1}$, e.g., greater than about 0.15 d$^{-1}$, e.g., greater than about 0.2 d$^{-1}$, e.g., greater than about 0.25 d$^{-1}$, e.g., greater than about 0.3 d$^{-1}$, e.g., greater than about 0.35 d$^{-1}$, etc. In another embodiment, the specific growth rate maintained by the continuous culture system described herein is less than about 1.0 d$^{-1}$, e.g., less than about 0.8 d$^{-1}$, e.g., less than about 0.7 d$^{-1}$, e.g., less than about 0.6 $d^{-1}$, e.g., less than about 0.5 $d^{-1}$, e.g., less than about 0.45 $d^{-1}$. In another embodiment, the specific growth rate may be maintained between about 0.1 $d^{-1}$ to about 0.45 $d^{-1}$. In one embodiment, the specific growth rate maintained by the continuous culture system described herein is between about 0.15 $d^{-1}$ to about 0.3 $d^{-1}$. In one embodiment, the specific growth rate maintained by the continuous culture system described herein is between about 0.2 $d^{-1}$ to about 0.25 $d^{-1}$.

As described above, the continuous culture system disclosed herein maintains a cell density less than about $2 \times 10^7$ cell/mL. A mechanism by which the cell densities may be maintained as described above involves maintaining a particular dilution rate to specific growth rate ratio. Chemostat cultures have dilution rates approximately equal to specific growth rates for a D/μ ratio of approximately 1. Perfusion cultures generally have higher absolute dilution rates and very low specific growth rates, so the D/μ ratio is significantly greater than 1. In the continuous culture system disclosed herein, however, a dilution rate that is slightly higher than specific growth rate preferably is maintained. Accordingly, in the continuous culture disclosed herein, a D/μ ratio greater than 1 is maintained. In particularly preferred embodiments, the dilution rate is calculated and set in accordance with the efficiency of the retention device so as to maintain the specific growth rate within a predetermined range. In one embodiment, the ratio of the dilution rate to the specific growth rate is greater than about 1.0, e.g., greater than about 1.2, e.g., greater than about 1.5, e.g., greater than about 2, e.g., greater than about 2.5. In another embodiment, the ratio of the dilution rate to the specific growth rate is less than about 5, e.g., less than about 4, e.g., less than about 3. In one embodiment, the ratio of D/μ is between about 1.2 and about 5. In another embodiment, the ratio of the dilution rate to the specific growth rate is between about 1.8 and about 3. In another embodiment, the ratio of the dilution rate to the specific growth rate is between about 2.0 and about 2.5.

The methods of the invention may be carried out in an appropriate culture unit or bioreactor. The bioreactor can be of any size as long as it is useful for culturing cells, e.g., mammalian cells. Since processes with low cell densities are generally easy to scale up, the methods of the invention may be particularly advantageous for large scale culturing (i.e., with culture volumes greater than 250 L) and may be particularly amenable to scaling up from small, laboratory scale cultures (e.g., 10 L) to production scale cultures (e.g., 250 L and greater) with minimal modification of culture conditions. The internal conditions of the culture unit, including but not limited to pH, $pO_2$, and temperature, are typically controlled during the culturing period. A production culture unit refers to the final culture unit used in the production of the polypeptide, virus, and/or any other product of interest. The volume of a large-scale production culture unit is generally greater than about 250 liters, and may be about 300, about 500, about 800, about 1000, about 2500, about 5000, about 8000, about 10,000, about 12,0000 L or more, or any intermediate volume. A suitable culture unit or production culture unit may be composed of (i.e., constructed of) any material that is suitable for holding cell cultures suspended in media under the culture conditions contemplated herein, and one that is conducive to mammalian cell growth and viability. Examples of suitable materials include, without limitation, glass, plastic, and/or metal. In preferred embodiments, the material(s) do not interfere, or do not significantly or do not substantially interfere, with expression and/or stability of the desired product, e.g., the polypeptide and/or virus of interest. One of skill in the art will be aware of, and will be able to choose, suitable culture units for use in practicing the present continuous culture system.

In some embodiments, the cell culture process is operated in more than one distinct culture units, such as using one or more seed (propagation) culture unit(s) followed by use of the production culture unit. In some embodiments, then, the process involves transferring about 50 L of the propagated seed culture (having about $1.0 \times 10^6$ cells/mL) into a 250 L culture unit containing about 150 L of culture medium. Generally, the continuous culture system described herein is applied only to production culture units. For example, seed mammalian cells may first be propagated, e.g., in batch, fed-batch, perfusion, and/or chemostat systems, in one or more seed culture units. After transfer of the cells to a production culture unit, the cells may be cultured according to the continuous culture system as described herein, e.g., with a cell retention device in a cell culture system having a dilution rate of less than about 2 $d^{-1}$ and a cell density of less than about $2 \times 10^7$ cell/mL.

Alternatively, expansion of the cells to the production culture unit and the production phase may be accomplished in one physical culture unit. For example, the cells may be expanded to a final production scale and the process switched to production conditions, whereupon the conditions for the continuous cell culture system described herein may be used.

It was unexpectedly discovered that the culture methods of the invention may be used to maintain cell densities and dilution rate within predetermined ranges, for example, to support production phases for a duration similar to that of chemostat or perfusion systems. By "predetermined ranges" is meant target ranges, e.g., ranges described herein for operation of the continuous culture systems according to embodiments of the instant invention. For example, in some embodiments, the target range for dilution rate is between 0.2 $d^{-1}$ to 2.0 $d^{-1}$ and the cell density is less than $2 \times 10^7$ cell/mL. In another embodiment, the dilution rate is maintained at less than 2.0 $d^{-1}$, e.g., less than 1.8 $d^{-1}$, e.g., less than 1.5 $d^{-1}$, or e.g., less than 1.2 $d^{-1}$, and the cell density is less than $1.5 \times 10^7$ cell/mL, e.g., less than $1 \times 10^7$ cell/mL, or e.g., less than $8 \times 10^6$ cell/mL. In some embodiments, the specific growth rate is 0.1 $d^{-1}$ to 1.0 $d^{-1}$ and the ratio of dilution rate to specific growth rate is between 1.2 and 5. In some embodiments, the target range for dilution rate is between 0.5 $d^{-1}$ to 1.0 $d^{-1}$ and the cell density is less than $5 \times 10^6$ cell/mL. In some embodiments, the specific growth rate is 0.15 $d^{-1}$ to 0.3 $d^{-1}$ and the ratio of dilution rate to specific growth rate is between 1.8 and 3. In some embodiments, the specific growth rate is 0.2 $d^{-1}$ to 0.25 $d^{-1}$ and the ratio of dilution rate to specific growth rate is between 2.0 and 2.5. In a particularly preferred embodiment, cell density is $5 \times 10^6$ cell/mL or less, dilution rate is less than 0.6 $d^{-1}$, and specific growth rate is 0.18 to 0.27 $d^{-1}$. In another particularly preferred embodiment, cell density is less than $5 \times 10^6$ cell/mL, dilution rate is between 0.55 and 0.6 $d^{-1}$, and specific growth rate is 0.16 to 0.26 $d^{-1}$. Embodiments include maintaining the dilution rate and/or cell density and/or specific growth rate and/or ratio of dilution rate to specific growth rate within a target range (e.g., those set forth above) for at least about 50%, e.g. at least about 60%, e.g., at least about 70%, e.g., at least about 80%, e.g., at least about 90%, e.g., at least about 95%, e.g., at least about 98% of the total continuous culture time and/or production phase time.

The continuous cell culture system described herein can allow sustained production of a polypeptide and/or virus of interest from mammalian cells. In some embodiments, the cells are cultured for a total continuous cell culture time of more than about 7 days. In more preferred embodiments, the cells are cultured for more than about 9 days, more than about 14 days, more than about 21 days, more than about 28 days, more than about 35 days, more than about 40 days, more than about 45 days, or more than about 50 days.

The terms "cell culture medium" and "culture medium" (or simply "medium") refer to a nutrient solution used for growing eukaryote cells that typically provides at least one component from one or more of the following categories: (1) salts (e.g., sodium, potassium, magnesium, calcium, etc.) contributing to the osmolality of the medium; (2) an energy source, usually in the form of a carbohydrate such as glucose; (3) all essential amino acids, and usually the basic set of twenty amino acids; (4) vitamins and/or other organic compounds required at low concentrations; and (5) trace elements, where trace elements are defined as inorganic compounds that are typically required at very low concentrations, usually in the micromolar range. The nutrient solution may optionally be supplemented with one or more of the components from any of the following categories: (a) animal serum; (b) hormones and other growth factors such as, for example, insulin, transferrin, and epidermal growth factor; and (c) hydrolysates of plant, yeast, and/or tissues, including protein hydrolysates thereof.

The present continuous culture system finds particular use when cultivating mammalian cells expressing a polypeptide and/or virus of interest in serum-free medium, chemically-defined medium, or medium lacking animal-derived components. Chemically defined media are media in which all components have a known chemical structure. Chemically-defined medium are available from commercial suppliers, such as, for example, Sigma, JRH Biosciences, Gibco and Gemini. In other embodiments of the invention, the medium may contain an amino acid(s) derived from any source or method known in the art, including, but not limited to, an amino acid(s) derived from adding one or more amino acids or adding a peptone or protein hydrolysate (including hydrolysate from an animal, yeast, or plant source(s)).

Any cell culture medium that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. In preferred embodiments, the culture medium lacks animal-derived components. As used herein, "animal-derived" components are any components that are produced in an intact animal (such as, e.g., proteins isolated and purified from serum), or produced using components produced in an intact animal (such as, e.g., an amino acid made by using an enzyme isolated and purified from an animal to hydrolyse a plant source material). By contrast, a protein which has the sequence of an animal protein (i.e., has a genomic origin in an animal) but which is produced in vitro in cell culture (such as, e.g., in a recombinant yeast or bacterial cells or in an established continuous eukaryote cell line, recombinant or not), using media lacking components produced in, or isolated and purified from, an intact animal is not an "animal-derived" component. For example, insulin produced in a yeast or a bacterial cell, or insulin produced in an established mammalian cell line, such as, e.g., CHO, BHK or HEK cells, or interferon produced in Namalwa cells, does not constitute an "animal-derived" component. Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants.

In yet other embodiments of the invention, the medium used during the cell growth phase contains concentrated medium, i.e., medium that contains higher concentration of nutrients than is normally necessary and normally provided to a growing culture. One skilled in the art will recognize which cell media, inoculation media, etc. is appropriate to culture a particular cell, e.g., animal cells (e.g., CHO cells). For example, one of skill in the art will be able to suitably select for a particular culture the amount of glucose and other nutrients, such as glutamine, iron, trace elements, and the like, as well as other culture variables, such as, e.g., the amount of foaming, osmolality, etc. (see, e.g., Mather, J. P., et al. (1999) "Culture media, animal cells, large scale production," Encyclopedia of Bioprocess Technology: Fermentation, Biocatalysis, and Bioseparation, Vol. 2:777-785 (especially pages 780 to 783); U.S. Patent Application Publication No. 2006/0121568 (especially paragraphs [0144] to [0185] and [0203] to [0331]); both of which are hereby incorporated by reference herein in their entireties). The present invention also contemplates variants of such known media, including, e.g., nutrient-enriched variants of such media, concentrated media, chemically-defined media, serum-free media, and media otherwise modified in accordance with various embodiments of the invention.

The continuous culture system is not limited to any type of non-anchorage dependent mammalian cells. The mammalian cells may be genetically modified mammalian cells expressing a recombinant polypeptide (and/or recombinant virus) of interest, or unmodified mammalian cells expressing a polypeptide (and/or virus) of interest. A number of mammalian cell lines are suitable host cells for recombinant expression of polypeptides and/or viruses. Mammalian host cell lines include, for example, COS, PER.C6, TM4, VERO, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. Any mammalian cells that can be adapted for suspension culture may be used in the disclosed cell culture method. A nonlimiting example includes CHO cells, which are anchorage dependent when cultivated in the presence of serum and suitable surfaces, but are easily adapted to growth in suspension culture (see, e.g., Rasmussen 1998, Cytotechnology 28: pp 31-42, especially pages 34-37, regarding culturing a serum-free CHO cell line). Also any mammalian cell capable of expressing the polypeptide and/or virus of interest (whether produced recombinantly or not) may be used in the disclosed cell culture methods. In one embodiment, the continuous cell culture method disclosed herein may be used to adapt an anchorage dependent cell line to a non-anchorage dependent cell line. Numerous cell lines are available from commercial sources such as the American Type Culture Collection (ATCC). In one embodiment, the continuous cell culture system is used to culture genetically modified CHO cells.

As described herein, the continuous cell culture system allows for recovery of a polypeptide and/or virus of interest (e.g., a recombinant polypeptide and/or recombinant virus). The polypeptide and/or virus typically is recovered from spent medium that has been removed from the system. Advantages of preferred embodiments of the invention include reducing the residence time of the protein and/or virus in the bioreactor, which is particularly useful for products susceptible to degradation. However, the continuous cell culture system as disclosed herein is not limited to such labile polypeptides or viruses, and may be used for the recovery of other polypeptides or viruses of interest.

The present invention relates to methods for the improved large-scale continuous culture of mammalian cells that express one or more proteins and/or viruses of interest, whether from endogenous genes or natural infection, or subsequent to introduction into such cells of recombinant genes encoding the protein or virus of interest. Such proteins include, as nonlimiting examples, enzymes, hormones, antibodies, protein receptors, fusion proteins (e.g., fusions of soluble receptors and the Fc domain of an IgG), vaccines, cytokines, chemokines, growth factors, blood factor proteins etc. In one embodiment, the protein of interest is ADAMTS13. In another embodiment, the protein of interest is Factor VII or Factor VIII. In another embodiment, the protein of interest is alpha-1-proteinase inhibitor.

The present invention also relates to methods for the improved large-scale continuous culture of mammalian cells that express one or more viruses of interest (including viral particles and viral vectors), whether wildtype or recombinant. Nonlimiting examples of such wildtype or recombinant viruses, viral particles and/or viral vectors include Adenoviruses, Herpes viruses, Retroviruses, Lentiviruses, Influenza viruses, etc. Production of recombinant viruses, viral particles, and use of recombinant viral vectors are well-known in the art. For the expression of virus, the method according to the invention is particularly suitable for, but not limited to, infection with and expression of non-lytic viruses such as e.g. Hepatitis A and TBE in, e.g., Vero cells, or Lentivirus in, e.g., HEK293 or other human or mammalian cell lines.

Once the medium has been removed from the culture unit, it may be subjected to one or more processing steps to obtain the protein and/or virus of interest. Downstream processing steps include, without limitation, centrifugation and/or filtration to remove cells not previously withdrawn from the culture; affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), extraction, and the like. See, generally, Scopes, Protein Purification, Springer-Verlag, New York, 1982; and Protein Purification, J.-C. Janson and Lars Ryden, editors, VCH Publishers, New York, 1989.

In certain embodiments, the mammalian cells are subjected to a pre-culturing step, e.g., a pre-culturing step of adapting the cells for production of the polypeptide and/or virus of interest. In some embodiments, the adapting comprises pre-culturing the cells in suspension, e.g., for a time to allow the culture to reached a desired final working volume, e.g., of about 5 L, about 8 L, about 10 L, about 12 L, about 15 L, or about 20 L, etc. At this point, the culture can be switched to a continuous medium feed and operated according to the continuous cell culture system described herein.

Exemplary embodiments of the invention disclosed herein are further discussed in the Examples provided below. The Examples, however, and their particular details, are in no way intended to limit the invention.

EXAMPLES

Example 1

Chemostat cultures were prepared with a recombinant CHO cell line expressing human ADAMTS13 in chemically defined BACD-A 13 medium (enriched DMEM/F12 formulation), which is supplemented as shown in Table 1.1.

TABLE 1.1

Composition of cell culture medium BACD-A13

| Component | Concentration [g/kg] |
| --- | --- |
| DMEM/HAMS F12 BaxS9 | 12.74 |
| L-Glutamine | 1.3 |
| Synperonic | 1.00 |
| Ethanolamin | 0.00153 |
| ZnSO4•7H2O | 0.001 |
| NaHCO3 | 1.5 |

Recombinant CHO cells expressing human ADAMTS13 were adapted to a chemically-defined medium, namely BCS medium, as shown in Table 1.2.

TABLE 1.2

Composition of cell culture medium BCS

| Component | Concentration [g/kg] |
| --- | --- |
| DMEM/HAMS F12 Bax Special | 11.75 |
| L-Glutamin | 0.9 |
| Synperonic | 1.00 |
| Ethanolamin | 0.00153 |
| Putrescine•2HCl | 0.0036 |
| FeSO4•7H2O | 0.0006 |
| NaHCO3 | 2.0 |

A Development Working Cell Bank was thawed and cell inoculum was prepared in BCS medium. Cells were transferred to a 10 L culture unit with Rushton type impellers and cultivated in repeated batch cultures in BACD-A13 medium with inline controlled parameters, as follows: pH 7.10, temperature 36° C., and DO 20% air saturation.

After 2 batch cycles, cultures reached a final working volume of 10 L, and the culture was switched to continuous medium feed on day 4 and operated until day 18 in a chemostat mode.

From this culture, a second 10 L culture unit with Rushton type impeller and a cell retention device was inoculated for chemostat-like perfusion, using the same cell culture medium, and cultivated for 8 days in repeated batch culture. CYTOPORE 2™ Microcarriers (GE Healthcare) were added (0.25 g/L), and the culture unit was further operated in continuous chemostat-like perfusion mode in parallel to the other culture unit in chemostat mode. Culture units were agitated with Rushton type impellers with baffles at 140 rpm, which corresponds to a specific power/volume input of approximately 40 W/m$^3$.

Both culture units were operated in parallel for 24 days. Data were calculated in 3 weekly intervals and an additional 3 day interval (Table 1.3. (Chemostat) and Table 1.4 (Chemostat-like perfusion). Data from four intervals of Table 1.3. (days 26-32; days 33-39; days 40-46; and days 47-49) were directly compared with the four intervals shown in Table 1.4 (days 9-15; days 16-22; days 23-29; and days 30-32).

Samples from the culture units were taken and analysed for ADAMTS13 concentration by ELISA, and ADAMTS13 activity by FRETS-73 assay. Cell counts were determined by Nucleocounter technology. For perfusion cultures, total cell counts and cell counts in the supernatant were measured separately to calculate the relative cell retention. Dilution rates were measured and used for calculating growth rates and volumetric productivities. The equations are provided below Growth rate ($\mu$) in the chemostat culture was calculated using the equation: $\mu = D + \ln(X_t/X_{t-1})/(t-t_{-1})$, wherein D=Dilution rate, $X_t$=Total cell density at time t, and $(t-t_{-1})$=Time between t and $t_{-1}$.

Growth rate ($\mu$) in the chemostat-like perfusion culture was calculated using the equation $\mu = \ln(X_t/X_{t-1})/(t-t_{-1}) + D \times (\log \text{ mean } X_{SN}/\log \text{ mean } X)/(t-t_{-1})$; wherein D=Dilution rate, $X_t$=Total cell density at time t, $(t-t_{-1})$=Time between t and $t_{-1}$, log mean X=logarithmic mean of total cell density= $(X_t - X_{t-1})/(\ln(X_t) - \ln(X_{t-1}))$, and log mean $X_{SN}$= logarithmic mean of cell density supernatant.

Cell retention rate was calculated as=$100 \times (1 - X_{SN}/X)$ [%]

As noted above, after inoculating the culture unit with a cell retention device, on day 18, cells were further cultivated in a continuous chemostat-like perfusion mode. Due to the cell retention, cell density in the chemostat-like perfusion cultures were increased. However due to the relatively low cell retention rate (mean 72%; range 60%-84%) the cell densities were maintained at a relatively low level of $<1 \times 10^7$ cells/mL (mean $4.93 \times 10^6$ cells/mL) and the maximum dilution rate was 0.62 $d^{-1}$.

The low cell retention rate also allowed the cells to maintain a continuous specific growth rate of 0.18-0.27 $d^{-1}$ without leading to excessive cell densities. This is considered an advantage for recombinant cells, which express recombinant proteins in a growth associated manner. Despite a reduced specific productivity (e.g. 974 mU/E06/d vs. 1400 mU/E06/d) the volumetric productivity was increased by over 70% from 2648 U/L/d to 4538 U/L/d due to the approximately 2.8 fold higher cell density. The specific activity of the recombinant protein also improved (941 U/mg vs. 834 U/mg), probably due to the reduced residence time in the culture unit, thereby improving stability, or any other beneficial effect on the structure and function of the expressed recombinant ADAMTS13.

TABLE 1.3

Fermentation Suspension Data for Chemostat Culture

| Interval Days | ZZ.-Nuc. [1 E6/ml] | D [1/d] | $\mu$ [1/d] | Adamts Frets [mU/ml] | Adamts ELISA [µg/ml] | spec. Activity U/mg | P Frets [U/L/d] | P ELISA [mg/L/d] | qp Frets [mU/E06/d] | qp ELISA [µg/E06/d] |
|---|---|---|---|---|---|---|---|---|---|---|
| 0-4 | n.a. | Batch | 0.420 | n.a. | n.a. | n.a. | n.a. | n.a. | n.a. | n.a. |
| 5-11 | 2.76 | 0.353 | 0.369 | 4314.4 | 4.09 | 1055 | 1523 | 1.44 | 551 | 0.52 |
| 12-18 | 2.01 | 0.309 | 0.299 | 9148.8 | 8.45 | 1083 | 2830 | 2.61 | 1407 | 1.30 |
| 19-25 | 1.82 | 0.311 | 0.300 | 8609.6 | 8.67 | 993 | 2677 | 2.70 | 1473 | 1.48 |
| 26-32 | 1.76 | 0.309 | 0.304 | 8868.2 | 9.96 | 891 | 2742 | 3.08 | 1560 | 1.75 |
| 33-39 | 1.84 | 0.321 | 0.337 | 7845.4 | 10.10 | 777 | 2519 | 3.24 | 1369 | 1.76 |
| 40-46 | 1.97 | 0.330 | 0.340 | 8098.7 | 9.24 | 877 | 2674 | 3.05 | 1358 | 1.55 |
| 47-49 | 2.02 | 0.361 | 0.343 | 7353.7 | 9.30 | 791 | 2658 | 3.36 | 1314 | 1.66 |
| Mean 26-49 | 1.90 | 0.330 | 0.331 | 8041.5 | 9.65 | 834 | 2648 | 3.18 | 1400 | 1.68 |

TABLE 1.4

Fermentation Suspension Data for Chemostat-like culture

| nterval Days | Total CC [1 × 10 E6/ml] | CC Supernatant. [1 × 10 E6/ml] | Cell retention % | D [1/d] | $\mu$ [1/d] | Adamts Frets [mU/ml] | Adamts ELISA [µg/ml] | spec. Activity U/mg | P Frets [U/L/d] | P ELISA [mg/L/d] | In qp Frets [mU/E06/d] | In qp ELISA [mU/E06/d] |
|---|---|---|---|---|---|---|---|---|---|---|---|---|
| 0-8 | n.a. | n.a. | n.a. | Batch | 0.398 | n.a. | n.a. | n.a. | n.a. | n.a. | n.a. | n.a. |
| 9-15 | 2.04 | 0.82 | 60 | 0.37 | 0.271 | 5804.4 | 6.25 | 929 | 2176 | 2.34 | 1068 | 1.15 |
| 16-22 | 3.75 | 1.14 | 70 | 0.44 | 0.192 | 8863.5 | 10.18 | 871 | 3889 | 4.46 | 1037 | 1.19 |
| 23-29 | 5.86 | 1.53 | 74 | 0.53 | 0.178 | 11873.6 | 11.03 | 1076 | 6292 | 5.84 | 1073 | 1.00 |
| 30-32 | 8.05 | 1.30 | 84 | 0.62 | 0.175 | 9398.6 | 10.61 | 886 | 5794 | 6.54 | 719 | 0.81 |
| Mean 9-32 | 4.93 | 1.20 | 72 | 0.49 | 0.204 | 8985.0 | 9.52 | 941 | 4538 | 4.80 | 974 | 1.04 |

The specific growth rate of the cells in batch culture was about 0.42 $d^{-1}$. After switching to chemostat culture, a decline of the specific growth rate to approximately 0.30 $d^{-1}$ was observed, which is indicative for growth limiting conditions in the chemically-defined medium. Cell densities equilibrated in the range of $1.8-2 \times 10^6$ cells/mL. Under such continuous culture conditions, the steady state was reached (beginning in the interval 12-18), and over 2500 U/L/d can be achieved.

Example 2

Chemostat cultures were prepared with a recombinant CHO cell line expressing human ADAMTS13 in chemically-defined BACD-A13 medium (enriched DMEM/F12 formulation), which is supplemented as shown in Table 1.1.

Recombinant CHO cells expressing human ADAMTS13 were adapted to a chemically-defined medium, namely BCS medium, as shown in Table 1.2. A Development Working Cell Bank was thawed and cell inoculum was prepared in BCS medium. Cells were transferred to a 1.5 L culture unit with blade impellers and cultivated in repeated batch cultures in BACD-A13 medium with inline controlled pH 7.1, temperature 36° C., and DO 20% air saturation.

After 2 batch cycles, cultures reached a final working volume of 1.5 L, and the culture was switched to continuous medium feed on day 5 and operated until day 7 in a chemostat mode.

From this culture a second culture unit comprising a cell retention device with blade impellers was inoculated using the same cell culture medium and cultivated for 1 day in batch culture. CYTOPORE 2™ Microcarriers (GE Healthcare) were added (0.25 g/L), and the culture unit was further operated in continuous chemostat-like perfusion mode in parallel to the other culture unit in chemostat mode.

Both culture units were operated in parallel for 28 days. Data were calculated in 4 weekly intervals (Table 2.1 (chemostat) and 2.2 (chemostat-like perfusion mode)).

Samples from the culture units were taken and analysed for ADAMTS13 concentration by ELISA and ADAMTS13 activity by FRETS-73 assay. Cell counts were determined by Nucleocounter technology. For chemostat-like perfusion cultures, total cell counts and cell counts in the supernatant were measured separately to calculate the relative cell retention. Dilution rates were measured and used for calculation of growth rates and volumetric productivities.

Growth rate (i) in the chemostat culture was calculated using the equation: $\mu = D + \ln(X_t/X_{t-1})/(t-t_{-1})$, wherein D=Dilution rate, $X_t$=Total cell density at time t, and $(t-t_{-1})$=Time between t and $t_{-1}$.

Growth rate (μ) in the chemostat like perfusion culture was calculated using the equation $\mu = \ln(X_t/X_{t-1})/(t-t_{-1}) + D \times$ (log mean $X_{SN}$/log mean $X$)/$(t-t_{-1})$; wherein D=Dilution rate, $X_t$=Total cell density at time t, $(t-t_{-1})$=Time between t and $t_{-1}$, log mean X=logarithmic mean of total cell density= $(X_t - X_{-1})/(\ln(X_t) - \ln(X_{t-1}))$, and log mean $X_{SN}$= logarithmic mean of cell density supernatant.

Cell retention rate was calculated as=$100 \times (1 - X_{SN}/X)$ [%]

TABLE 2.1

Fermentation Suspension Data for Chemostat Culture

| Interval Days | Total CC [1 × 10 E6/ml] | D [1/d] | μ [1/d] | Adamts Frets [mU/ml] | Adamts ELISA [μg/ml] | spec. Activity U/mg | P Frets [U/L/d] | P ELISA [mg/L/d] | qp Frets [mU/E06/d] | qp ELISA [μg/E06/d] |
|---|---|---|---|---|---|---|---|---|---|---|
| 0-5 | n.a. | Batch | 0.507 | n.a. | n.a. | n.a. | n.a. | n.a. | n.a. | n.a. |
| 9-15 | 1.87 | 0.345 | 0.340 | 2879.8 | 2.987 | 964 | 994.0 | 1.031 | 533.0 | 0.553 |
| 16-22 | 1.21 | 0.298 | 0.253 | 3483.7 | 3.755 | 926 | 1042.9 | 1.123 | 867.7 | 0.933 |
| 23-29 | 1.02 | 0.270 | 0.262 | 3726.6 | 3.928 | 946 | 951.8 | 1.008 | 957.9 | 1.021 |
| 30-36 | 0.83 | 0.279 | 0.268 | 2551.1 | 2.858 | 895 | 691.8 | 0.780 | 837.7 | 0.948 |
| Mean 9-36 | 1.23 | 0.298 | 0.281 | 3160.3 | 3.382 | 933 | 920.1 | 0.986 | 799.1 | 0.864 |

TABLE 2.2

Fermentation Suspension Data for Chemostat-like Perfusion Culture

| Interval Days | Total CC [1 × 10 E6/ml] | CC Supernatant. [1 × 10 E6/ml] | Cell retention % | D [1/d] | μ [1/d] | Adamts Frets [mU/ml] | Adamts ELISA [μg/ml] | Spec.z. Activity U/mg | P Frets [U/L/d] | P ELISA [mg/L/d] | q Frets [mU/E06/d] | q ELISA [μg/E06/d] |
|---|---|---|---|---|---|---|---|---|---|---|---|---|
| 02-08 | 1.96 | 1.22 | 38 | 0.449 | 0.262 | 2767.4 | 3.180 | 870 | 1241.6 | 1.427 | 634.6 | 0.729 |
| 09-15 | 2.95 | 1.12 | 62 | 0.442 | 0.256 | 4726.5 | 4.788 | 987 | 2090.0 | 2.117 | 707.7 | 0.717 |
| 16-22 | 3.90 | 1.06 | 73 | 0.592 | 0.207 | 3855.3 | 4.071 | 947 | 2281.5 | 2.409 | 585.6 | 0.618 |
| 23-29 | 3.57 | 1.00 | 72 | 0.604 | 0.205 | 2671.2 | 3.027 | 882 | 1613.4 | 1.829 | 451.8 | 0.512 |
| 30-36 | 3.52 | 1.13 | 68 | 0.594 | 0.222 | 2559.4 | 2.761 | 927 | 1519.5 | 1.639 | 431.3 | 0.465 |
| 37-43 | 4.20 | 1.18 | 72 | 0.571 | 0.219 | 2828.7 | 2.905 | 974 | 1615.2 | 1.659 | 384.7 | 0.395 |
| 44-49 | 4.30 | 1.21 | 72 | 0.566 | 0.159 | 2705.0 | 3.110 | 870 | 1530.0 | 1.759 | 355.9 | 0.409 |
| Mean 02-29 | 3.09 | 1.10 | 61 | 0.522 | 0.232 | 3505.1 | 3.767 | 922 | 1806.6 | 1.945 | 594.9 | 0.644 |
| Mean 02-49 | 3.49 | 1.13 | 68 | 0.545 | 0.219 | 3159.1 | 3.406 | 922 | 1698.8 | 1.834 | 507.3 | 0.549 |

The specific growth rate of the recombinant CHO cells expressing ADAMTS-13 in batch culture was about 0.51 $d^{-1}$. After switching to chemostat culture, a decline in the specific growth rate to less than 0.30 $d^{-1}$ was observed, which is indicative of growth limiting conditions in the chemically-defined medium. Cell densities equilibrated in the range of 0.8-1.2×10⁶ cells/mL with a specific growth rate of 0.25-0.27 $d^{-1}$. Under such continuous culture conditions, the steady state was reached (beginning in the interval 16-36). The mean productivity of all 4 intervals from day 09-36 was 920 U/L/d.

As described above, after inoculating the culture unit with a cell retention device on day 7, cells were further cultivated in continuous chemostat-like mode. Data from four intervals (days 9-15; days 16-22; days 23-29; and days 30-36) and the mean value of days 9-36 of Table 2.1 were directly compared with the data from four intervals (days 2-8; days 9-15; days 16-22; and days 23-29) and the mean value of days 2-29 of Table 2.2.

The chemostat-like perfusion culture was then operated (without a chemostat as reference) for another 3 intervals (days 30-36; days 37-43; and days 44-49) to demonstrate the long term stability of the chemostat-like perfusion culture. Mean values of 7 weeks of continuous culture are provided in Table 2.2 (mean of days 2-49).

Due to the cell retention, cell density in the perfusion cultures increased. However due to the relatively low cell retention rate (mean of days 02-29:61%, mean of days 02-49:68%. range 38%-72%) the cell densities were maintained at the relatively low level of <5×10⁶ cells/mL (mean of days 02-49=3.49×10⁶ cells/mL). The maximum dilution rate of approximately 0.60 $d^{-1}$ was reached in the 3rd interval and then remained constant between 0.55 $d^{-1}$-0.60 $d^{-1}$ until the end of the experiment (mean of days 02-49:0.55 $d^{-1}$).

The low cell retention rate also allowed the cells to maintain a continuous specific growth rate of 0.16-0.26 $d^{-1}$ (mean of days 02-49:0.22 $d^{-1}$) without leading to excessive cell densities. Despite a reduced specific productivity (e.g. 595 mU/E06/d vs. 799 mU/E06/d) the volumetric productivity was increased by over 90% from 920 U/L/d to 1807 U/L/d (mean of first 4 intervals) due to the approximately 2.8× higher cell density. The productivity of the chemostat-like culture remains relatively stable in the range from 1500-1600 U/L/d for the additional 3 intervals.

As in Example 1, it was demonstrated that this approach of stabilizing continuous suspension cultures with a lowered cell retention rate can compensate for the disadvantages of severe growth limitations under certain culture conditions (e.g., when using chemically-defined media). Accordingly, controlling cell retention allows the culture to be maintained at relatively moderate cell densities and relatively low and constant dilution rates. Also due to the relatively low cell retention rate, the culture retained more of the characteristics of a continuous suspension culture, as shown, e.g., by the specific growth rates.

All patents, patent publications, and other publications referred to herein are hereby incorporated by reference, to the same extent as if each individual publication, patent, or patent publication was specifically and individually indicated to be incorporated by reference.

Certain modifications and improvements will occur to those skilled in the art upon a reading of the foregoing description. It should be understood that all such modifications and improvements have been deleted herein for the sake of conciseness and readability. Nonetheless, all such modifications and improvements are contemplated as within the scope of the instant invention and are properly within the scope of the following claims.

The invention claimed is:

1. A method for producing a polypeptide of interest in a continuous cell culture, said method comprising
   (a) culturing mammalian cells genetically modified to express the polypeptide of interest in a continuous cell culture system, wherein said cell culture system has a dilution rate (D) of less than 0.6 $d^{-1}$, a ratio of the dilution rate to a specific growth rate (D/μ) of from 1.2 to 5, and a cell density of less than 5×10⁶ cell/mL; and
   (b) recovering the polypeptide of interest from culture medium removed from the cell culture system.

2. The method of claim 1, wherein the cells are CHO cells.

3. The method of claim 1, wherein the polypeptide of interest is a disintegrin-like and metallopeptidase with thrombospondin type 1 motif 13 (ADAMTS13) protein.

4. The method of claim 1, wherein the culture system further comprises a cell retention device that produces a cell retention rate of from 50% to 90%.

5. The method of claim 1, wherein said cells are cultured in a serum-free medium.

6. The method of claim 2, wherein the polypeptide of interest is a disintegrin-like and metallopeptidase with thrombospondin type 1 motif 13 (ADAMTS13) protein.

7. The method of claim 2, wherein the culture system further comprises a cell retention device that produces a cell retention rate of from 50% to 90%.

8. The method of claim 2, wherein said cells are cultured in a serum-free medium.

9. The method of claim 3, wherein the culture system further comprises a cell retention device that produces a cell retention rate of from 50% to 90%.

10. The method of claim 3, wherein said cells are cultured in a serum-free medium.

11. The method of claim 4, wherein said cells are cultured in a serum-free medium.

12. The method of claim 6, wherein the culture system further comprises a cell retention device that produces a cell retention rate of from 50% to 90%.

13. The method of claim 6, wherein said cells are cultured in a serum-free medium.

14. The method of claim 7, wherein said cells are cultured in a serum-free medium.

15. The method of claim 9, wherein said cells are cultured in a serum-free medium.

16. The method of claim 12, wherein said cells are cultured in a serum-free medium.

17. The method of claim 1, wherein said cell culture system has a specific growth rate of between 0.15 $d^{-1}$ and 0.3 $d^{-1}$.

18. The method of claim 1, wherein said cells are cultured in said cell culture system for more than 40 days.

19. The method of claim 4, wherein said cell retention device comprises a macroporous microcarrier.

20. The method of claim 1, wherein said cells are cultured in at least 250 L of medium.

* * * * *